United States Patent
Todd, Jr.

(10) Patent No.: US 6,446,630 B1
(45) Date of Patent: Sep. 10, 2002

(54) CYLINDER FILLING MEDICAL OXYGEN CONCENTRATOR

(75) Inventor: Oliver E. Todd, Jr., Maumee, OH (US)

(73) Assignee: Sunrise Medical HHG Inc, Longmont, CO (US)

( * ) Notice: Subject to any disclaimer, the term of this patent is extended or adjusted under 35 U.S.C. 154(b) by 0 days.

(21) Appl. No.: 09/499,201

(22) Filed: Feb. 7, 2000

Related U.S. Application Data
(60) Provisional application No. 60/119,653, filed on Feb. 11, 1999.

(51) Int. Cl.$^7$ ............................ A61M 16/00; A62B 7/00
(52) U.S. Cl. ............................ 128/204.18; 128/204.23; 128/204.26; 128/205.24
(58) Field of Search .................. 128/204.23, 204.18, 128/204.26, 205.24, 206.27, 205.11, 201.21, 204.21

(56) References Cited

U.S. PATENT DOCUMENTS

| | | | |
|---|---|---|---|
| 4,457,303 A | 7/1984 | Durkan | 128/204.24 |
| 4,461,293 A | 7/1984 | Chen | 128/204.23 |
| 4,462,398 A | 7/1984 | Durkan et al. | 128/200.14 |
| 4,706,664 A | * 11/1987 | Snook et al. | 128/204.23 |
| 4,932,402 A | * 6/1990 | Snook et al. | 128/204.23 |
| 5,071,453 A | 12/1991 | Hradek et al. | 55/21 |
| 5,503,146 A | 4/1996 | Froehlich et al. | 128/204.23 |
| 5,551,419 A | 9/1996 | Froehlich et al. | 128/204.23 |
| 5,858,062 A | 1/1999 | McCulloh et al. | 95/8 |
| 5,979,440 A | * 11/1999 | Honkonen et al. | 128/200.24 |
| 5,988,165 A | 11/1999 | Richey, II et al. | 128/205.12 |
| 6,186,142 B1 | * 2/2001 | Schmidt et al. | 128/204.18 |
| 6,302,107 B1 | * 10/2001 | Richey et al. | 128/205.11 |

* cited by examiner

*Primary Examiner*—Aaron J. Lewis
*Assistant Examiner*—Darwin P. Erezo
(74) *Attorney, Agent, or Firm*—MacMillan, Sobanski & Todd, LLC

(57) ABSTRACT

Apparatus for use with a medical oxygen concentrator for supplying oxygen enriched air to a patient and to a cylinder filler. The apparatus includes a flow control valve which is controlled by a control circuit to deliver doses of oxygen enriched air to a patient during at least a portion of the patient's inhalation and to deliver oxygen enriched air to a circuit for filling a portable oxygen cylinder during the remainder of the time. In the event of a failure of the control circuit, the flow control valve delivers a continuous flow of oxygen enriched air to the patient. In the event of a failure of the oxygen concentrator, oxygen enriched air stored in the oxygen cylinder may be delivered to the patient.

17 Claims, 2 Drawing Sheets

CYLINDER FILLING MEDICAL OXYGEN CONCENTRATOR

CROSS-REFERENCE TO RELATED APPLICATIONS

Applicants claim priority to U.S. Provisional Patent Application Ser. No. 60/119,653 filed Feb. 11, 1999.

STATEMENT REGARDING FEDERALLY SPONSORED RESEARCH OR DEVELOPMENT

Not Applicable.

BACKGROUND OF THE INVENTION

The invention relates to oxygen concentrators for supplying medical oxygen to a patient and to fill a portable oxygen container.

Oxygen concentrators are commonly used for supplying supplemental oxygen to patients for medical purposes. Typically, an oxygen concentrator includes an air compressor which delivers a flow of pressurized, filtered air to a molecular sieve bed which passes oxygen while blocking the flow of nitrogen. The oxygen enriched air at an output from the molecular sieve bed is typically about 90% to 95% pure oxygen, with the remainder being primarily argon. The oxygen enriched air may be stored in an accumulator prior to delivery to a patient through a nasal cannula. Preferably, two molecular sieve beds are provided to achieve a continuous flow of oxygen enriched air. While one of the molecular sieve beds is separating nitrogen from air to produce oxygen enriched air, a reverse flow of oxygen enriched air is passed through the other molecular sieve bed to purge previously separated nitrogen from the molecular sieve bed. Periodically, the operating modes of the two molecular sieve beds are switched.

Recently, oxygen concentrators have been used to supply oxygen enriched air simultaneously to a patient and to a compressor or other pressure intensifier for filling a portable oxygen cylinder. The portable oxygen cylinder is used as a portable oxygen source, allowing the patient to be ambulatory. The oxygen concentrator must be sized to have a capacity to deliver more oxygen enriched air than is needed by the patient. The excess oxygen enriched air is compressed to a pressure as high as 3000 psig and the compressed oxygen enriched air is stored in the portable oxygen cylinder. Apparatus using an oxygen concentrator simultaneously for supplying a patient's supplemental oxygen needs and for filling a gaseous oxygen cylinder is illustrated, for example, in U.S. Pat. Nos. 5,858,062 and 5,988,165. Such apparatus is designed to prioritize the usage of the available oxygen enriched air so that oxygen enriched air at a sufficiently high flow rate and/or at a sufficient concentration level is continuously delivered to the patient before any oxygen enriched air can be delivered to the compressor for filling a cylinder.

It is also known that the oxygen enriched air from an oxygen concentrator can be compressed and chilled to the point that it is liquefied for filling portable dewars sometimes used by ambulatory patients requiring supplemental oxygen. As used herein, the term "cylinder" is intended to include both portable gaseous oxygen cylinders and portable dewars for holding liquefied oxygen.

It is now well known that delivering a continuous flow of supplemental oxygen to a patient is wasteful of oxygen. Only the oxygen delivered to the patient during the initial part of the inhalation time reaches the portions of the patient's lungs where the oxygen is used by the patient. Oxygen in the trailing portion of the inhalation cycle remains in the portions of the patient's airway where it is not used. Also, any oxygen delivered to the patient while the patient exhales flows to the atmosphere without any benefit to the patient. Oxygen dose flow controllers are well known for conserving oxygen by delivering a short duration oxygen dose either only during inhalation or only during the initial portion of the inhalation cycle. Such flow controllers are shown, for example, in U.S. Pat. Nos. 5,370,112, 4,971,049, 4,519,387, 4,462,398, 4,461,293 and 4,457,303. Typically, the dose flow controllers either sense or anticipate the beginning of inhalation and deliver a short duration dose of oxygen which lasts for no more than the inhalation time and frequently for less than the entire inhalation time. When a dose flow controller is used by an ambulatory patient with a portable oxygen source, the oxygen source can supply oxygen for at least twice the time as apparatus which supplies a continuous flow of oxygen. Alternately, a dose flow controller can be used with a smaller capacity oxygen source, such as a smaller and lighter cylinder for portability or a smaller capacity oxygen concentrator.

BRIEF SUMMARY OF THE INVENTION

The one embodiment of the invention is directed to a medical oxygen concentrator suitable for supplying medical oxygen alternately to a patient and to a compressor for filling an oxygen cylinder for portable use by the patient. The oxygen concentrator is sized to have a continuous output flow rate at a concentration level which at least meets the needs of the patient. The output from the concentrator is delivered to a dose flow controller which senses when the beginning of a patient inhalation and momentarily opens a valve to deliver a dose of oxygen enriched air to the patient. During the time that the oxygen concentrator is not delivering a dose of oxygen enriched air to the patient, the flow controller delivers the oxygen enriched air from the oxygen concentrator to a cylinder filler circuit, such as a compressor and/or chiller for filling an oxygen cylinder with gaseous or liquefied oxygen enriched air. When patient inhalation is again sensed, delivery of oxygen enriched air from the concentrator to the cylinder filler circuit is interrupted and another oxygen dose is delivered to the patient. Preferably, the oxygen enriched air intermittently delivered to the cylinder filler circuit is at a greater flow rate than that continuously used by the compressor. The excess oxygen enriched air is accumulated to provide a continuous source of oxygen enriched air for the compressor. Alternately, the compressor can be controlled in response to the amount of oxygen enriched air available.

According to a further embodiment of the invention, a cylinder filler oxygen concentrator is provided with fail safe features for accommodating a patient's continuing oxygen needs. The oxygen concentrator is adapted to supply supplemental oxygen enriched air to the patient and for filling a cylinder. In the event of an operation failure of the oxygen concentrator, a valve may be opened to supply supplemental oxygen enriched air from the previously filled cylinder to the patient and an alarm may be sounded to call for help or to alert the patient. If a dose flow controller is used for controlling delivery of oxygen enriched air to the patient, a backup battery may be provided to extend the time that the cylinder can provide oxygen enriched air to the patient. Further, the dose flow controller also may be failsafe through a design which established a continuous flow of oxygen enriched air to the patient in the event of dose flow controller failing.

Various objects and advantages of the invention will become apparent from the following detailed description of the invention and the accompanying drawings.

DETAILED DESCRIPTION OF THE INVENTION

The present invention is directed to apparatus including an oxygen concentrator which is capable of delivering oxygen enriched air alternately to a patient and to a circuit for filling an oxygen cylinder. The oxygen enriched air output from an oxygen concentrator is connected through a dose flow controller for delivering doses of oxygen enriched air to the patient during at least a portion of the inhalation cycle. While the patient is exhaling and, preferably also during the trailing end portion of the inhalation cycle, the flow of oxygen enriched air is delivered to a cylinder filler, such as a compressor or other pressure intensifier for increasing the pressure to a level needed to fill a portable gaseous oxygen cylinder. Alternately, the gaseous oxygen cylinder is replaced with a dewar and the compressor includes a chiller for liquefying the oxygen enriched air.

Figure 1:
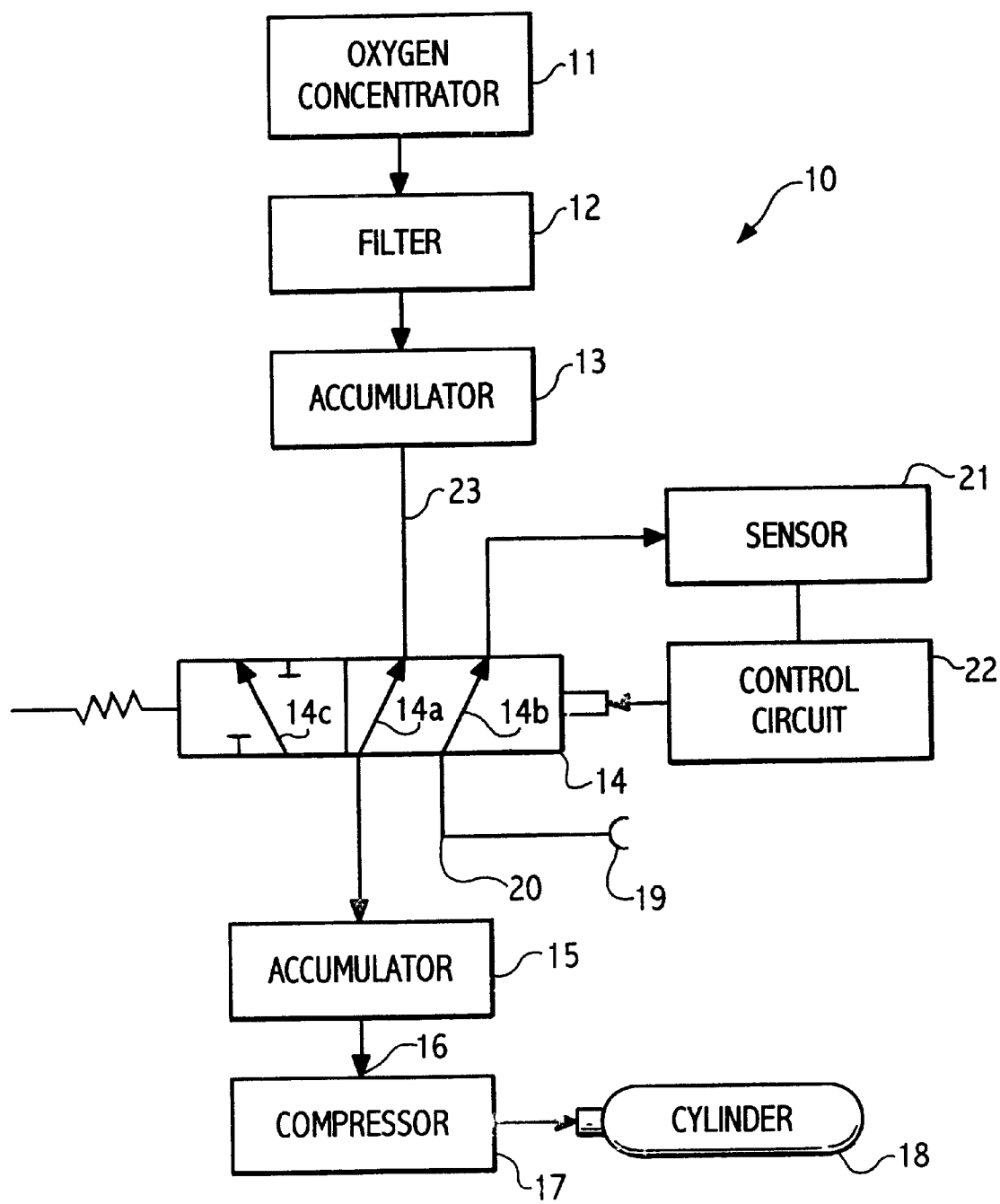
FIG. 1 is a block diagram illustrating apparatus for alternately delivering medical oxygen from an oxygen concentrator to a patient and to a compressor for filling a cylinder according to the invention.

Referring to FIG. 1, apparatus 10 is shown including a conventional oxygen concentrator 11 has an output which may be passed through an optional filter 12 to an optional accumulator 13. The filter 12 and accumulator 13 typically are an integral part of the oxygen concentrator 10. However, they also may be separate from the oxygen concentrator 10. The oxygen enriched air from the oxygen concentrator 11 is delivered via a line 23 to a two position flow control valve 14. In the illustrated first position of the valve, the line 13 is connected via a passage 14a to deliver oxygen enriched air to an optional accumulator 15 and thence to an input 16 to a compressor or pressure intensifier or chiller 17. The compressor 17 delivers the pressurized oxygen enriched air to fill an oxygen cylinder 18.

A nasal cannula 19 is connected via a hose 20 to the flow control valve 14. When the valve 14 is in the illustrated position, a passage 14b in the valve 14 connects the hose 20 to an inhalation sensor 21. The inhalation sensor 21 responds to a slight drop in pressure in the hose 20 when the patient begins to inhale at the nasal cannula 19. At the beginning of inhalation, the sensor 21 causes a control circuit 22 to move the flow control valve 14 to its second position. When in the second position, the connection from the valve 14 to the accumulator 15 is closed and the oxygen enriched air line 13 from the oxygen concentrator 10 is connected through a valve passage 14c to the line 20 for delivering a dose of oxygen enriched air through the line 20 and the nasal cannula 19 to the patient. After a predetermined time, the control circuit 22 returns the flow control valve 14 to its first position wherein oxygen enriched air is again delivered to the accumulator 15 and the compressor 17.

Some patients who require supplemental oxygen do not need supplemental oxygen for each breath. For these patients, the delivery of a dose of supplemental oxygen every second, every third or every fourth breath is adequate for achieving a desired blood oxygen saturation level. Oxygen dose flow controllers for portable oxygen systems frequently may be set to deliver a dose of oxygen to the nasal cannula only every second, every third or every fourth breath to further conserve oxygen and extend the ambulatory time. The control circuit 22 may include known technology for counting inhalation signals from the sensor 21 and for operating the flow control valve 14 only on every set number of inhalation cycles. With this arrangement, additional oxygen enriched air is available from the oxygen concentrator 11 for filling the cylinder 18.

Preferably, the flow control valve 14 is biased to the first position wherein oxygen enriched air is delivered to the nasal cannula 19 and required actuation by the control circuit 22 to move to the second position wherein the oxygen enriched air is delivered to the accumulator 15. With this arrangement, the valve 14 is released in response to the sensing of inhalation and is actuated a predetermined time after inhalation is sensed to stop delivery of an oxygen enriched air dose to the patient. This arrangement provides a failsafe operation in which oxygen enriched air will be continuously delivered to the patient in the event that either the inhalation sensor 21 or the control circuit 22 fails.

The oxygen enriched air may be delivered to the nasal cannula 19 for as little as less than half the inhalation time, to up to the full inhalation cycle with the same therapeutic effect as a constant flow of oxygen. However, it is preferable to deliver oxygen enriched air for less than the full inhalation cycle to minimize wasted oxygen. It also should be appreciated that the sensor 21 may be connected continuously to a nasal cannula for constantly monitoring patient breathing, for example, with a two hose nasal cannula. This permits accurate sensing of both the beginning of inhalation and the beginning of exhalation.

Since the oxygen enriched air is delivered only to the patient flow circuit or to the cylinder filler circuit at any given time, the oxygen concentrator only needs to have the continuous flow capacity to meet the patient's supplemental oxygen requirements. In prior art oxygen concentrator systems which were capable of delivering oxygen enriched air simultaneously to a patient and to a cylinder filling circuit, the oxygen concentrator needed to have a sufficient capacity to meet the simultaneous needs of both the patient flow circuit and the cylinder filler circuit. Further, they needed a prioritizing arrangement so that the patient was assured of receiving an adequate flow and concentration of oxygen enriched air before surplus oxygen enriched air could be delivered to the compressor circuit. Further, the dose flow control which includes the control circuit 22 and the valve 14 can be adjusted to provide different doses of oxygen enriched air during each inhalation or only during some inhalations, as is well known in the oxygen flow controller art. By providing only the dosage needed by the patient, additional oxygen enriched air is made available to the compressor 17 for more quickly filling the cylinder 18. Operation of the compressor 17 can be controlled based on the available oxygen enriched air.

The valve 14, the inhalation sensor 21 and the control circuit 22 may be, for example, of the type illustrated in U.S. Pat. Nos. 4,461,293, 4,462,398, 4,519,387 and 4,457,303, or of other commercially available designs. Or, the inhalation sensor 21 may include a circuit of the type used for generating a breathing signal in known bilevel CPAP (continuous positive airway pressure) therapy apparatus used for treating sleep apnea as shown, for example, in U.S. Pat. No. 5,551,419. The valve 14 may be of various known designs and constructions so long as it is capable of quickly and reliably connecting the oxygen enriched air flow from the concentrator to the patient at the beginning of inhalation and to the cylinder filling circuit at other times. It should be appreciated that the flow controller valve 14, the sensor 21 and the control circuit may be packaged with the oxygen concentrator 11, or that they may be packaged along with the accumulator 15 and the compressor 17 as separate apparatus which receives oxygen enriched air from any commercially available oxygen concentrator 11, and alternately delivers the oxygen enriched air to the patient or to a cylinder filler circuit.

Figure 2:
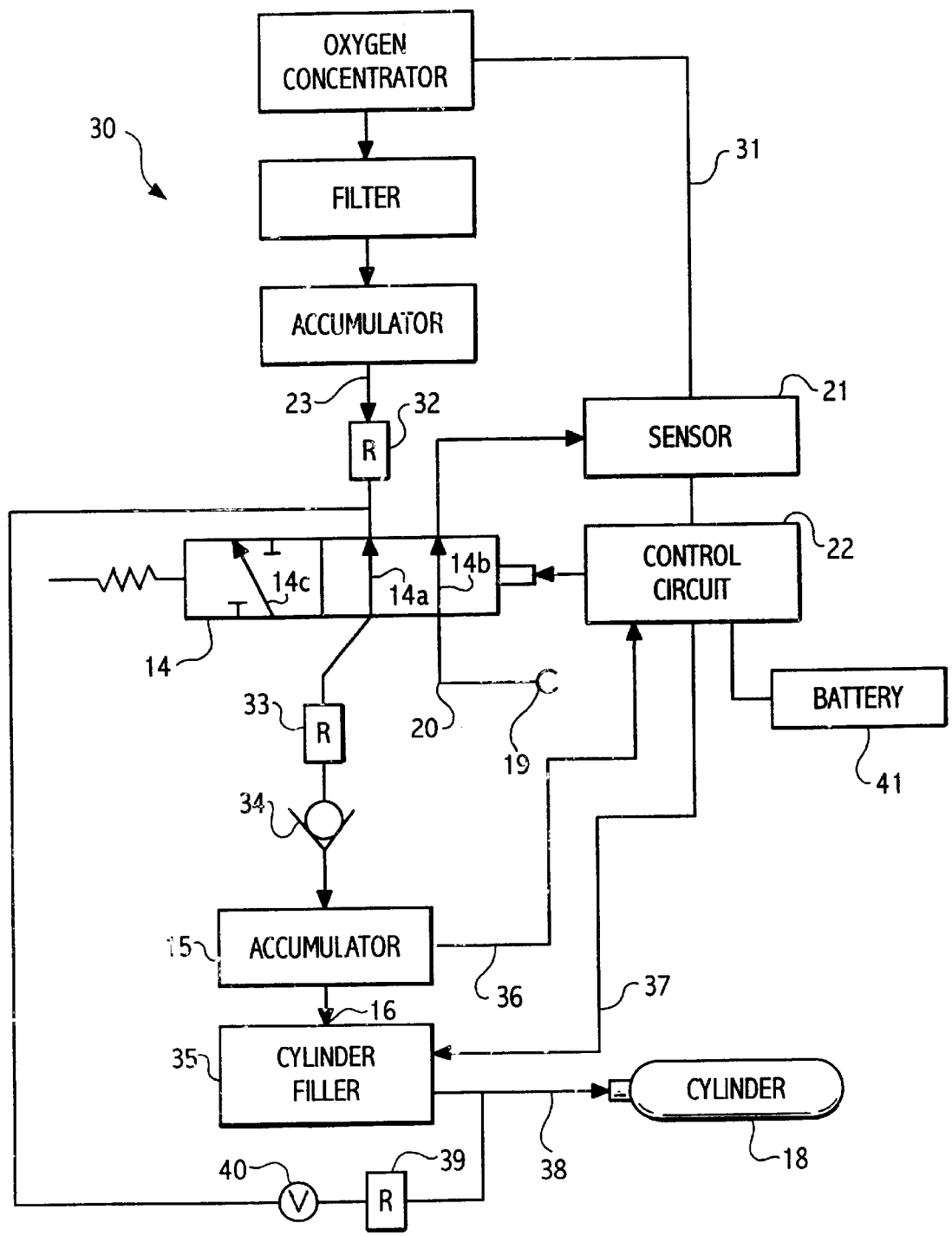
FIG. 2 is a block diagram illustrating apparatus for alternately delivering medical oxygen from an oxygen concentrator to a patient and to a compressor for filling an oxygen cylinder according to a modified embodiment of the invention.

FIG. 2 illustrates modified apparatus 30 for delivering oxygen enriched air to the nasal cannula 19 and to an oxygen cylinder 18. The same reference numbers have been assigned to components of the apparatus 30 of FIG. 2 which correspond with components of the apparatus 10 of FIG. 1. The oxygen concentrator 11 is provided with an integral oxygen concentration sensor (not shown) which can be, for example, of the type shown in U.S. Pat. No. 5,247,826 B. Alternately, an oxygen concentration sensor may be connected between the oxygen concentrator 11 and the valve 14. If an oxygen concentration sensor is provided, oxygen concentration data may be provided via a line 31 to the control circuit 22. A regulator 32 may be incorporated into the line 23 which delivers oxygen enriched air to the valve 14, or it may be an integral part of the oxygen concentrator 11. The regulator 32 can regulate the pressure of the oxygen enriched air delivered to the valve 14, and/or the oxygen enriched air flow rate. A regulator 33 and/or a check valve 34 may be connected between the valve 14 and the accumulator 15. The accumulator 15 is connected to a cylinder filler 35. As used herein, the term "cylinder filler" is intended to cover either a conventional electric motor driven gas compressor or a pressurized gas operated pressure intensifier connected to deliver high pressure oxygen enriched air to a compressed gas cylinder, or a chiller which produces and delivers liquefied oxygen enriched air to a dewar or other portable liquid oxygen container. Optionally, a gas pressure signal may be delivered on a line 36 from the accumulator 15 to the control circuit 22 to provide information on the gas pressure in the accumulator 15, and a control signal may be delivered from the control circuit 22 over a line 37 to the cylinder filler 35 for controlling operation of the cylinder filler 35.

In operation, the control circuit 22 may be programmed to prevent delivery of oxygen enriched air to the oxygen cylinder filler 35 until a predetermined oxygen concentration level is sensed. When an oxygen concentrator is first turned on, there is a delay before the product gas has a sufficiently high oxygen concentration. During this delay, the product gas may be continuously vented through the nasal cannula 19. Once an adequate oxygen concentration is produced, the valve 14 is positioned to deliver the oxygen enriched air to the accumulator 15 until patient inhalation at the nasal cannula 19 is detected by the sensor 21. Doses of oxygen enriched air are then delivered to the patient in response to the detection of each inhalation, or in response to the detection of selected inhalations, such as every second or every third inhalation. During the time that doses of oxygen enriched air are not delivered to the patient, the oxygen enriched air is delivered to the accumulator 15 and thence is delivered to the cylinder 18. If patient inhalation is not detected within a predetermined time, a continuous flow of oxygen enriched air may be delivered to the cannula 19 and an alarm may be sounded to notify the patient or to summons help.

Optionally, information on the gas pressure in the accumulator 15 can be used by the control circuit 22 for controlling the cylinder filler 35. For example, the cylinder filler 35 may be stopped when there is inadequate gas pressure in the accumulator 15. Alternately, if the cylinder filler 35 is a compressor, the speed of the compressor may be varied in response to the accumulator pressure so that the amount of oxygen enriched gas removed from the accumulator 15 is varied to maintain the accumulator pressure at a desired level or within a desired range. In the event that the circuitry for delivering doses of oxygen enriched air to the patient fails, the valve 14 will default to its failsafe position which delivers a continuous flow of oxygen enriched air to the nasal cannula 19. The resulting pressure reduction in the accumulator 15 will result in the cylinder filler 35 being stopped.

The cylinder filler 35 is connected through a line 38 to fill the cylinder 18. Optionally, the line 38 may be connected through a regulator 39 and a valve 40 to the line 23 between the accumulator 13 and the valve 14. Further, the control circuit 22 may include a power source operated by a battery 41 so that the valve 14 will be operated to deliver doses of oxygen enriched air to the patient during power failures. The valve 40 is of the normally open type and is connected to the power source for the oxygen concentrator 11 to be closed while the oxygen concentrator 11 is operating. In the event that the oxygen concentrator 11 stops due to a power failure or due to a mechanical failure, the valve 40 automatically opens and pressurized oxygen enriched air is delivered from the cylinder 18 through the pressure regulator 39 and the valve 40 to the flow control valve 14. The battery power will continue to operate the inhalation sensor 21 and the control circuit 22 to continue to deliver oxygen doses to the patient during the power failure. If the control circuit 22 also fails, oxygen enriched air will continuously flow from the cylinder 18 to the patient until the contents of the cylinder 18 are exhausted. It should be appreciated that this arrangement also will allow the oxygen concentrator to be stopped and moved with the patient to another room without an interruption in the delivery of oxygen enriched air to the patient. It also should be appreciated that a battery operated alarm (not shown) may be provided for operation whenever the valve 40 is open and oxygen enriched air is supplied from the cylinder 18.

It will be appreciated that various modifications and changes may be made to the above described preferred embodiment of a cylinder filling medical oxygen concentrator without departing from the scope of the following claims.

What is claimed is:

1. Apparatus for filling a cylinder with oxygen enriched air from a medical oxygen concentrator and for delivering oxygen enriched air to a patient comprising, in combination, a nasal cannula adapted to deliver a flow of oxygen enriched air from the oxygen concentrator to a patient, a cylinder, a cylinder filler circuit adapted to fill said cylinder with oxygen enriched air from the oxygen concentrator, a flow control valve having an inlet adapted to receive oxygen enriched air from the oxygen concentrator and having first and second positions, said flow control valve delivering oxygen enriched air from the oxygen concentrator to said nasal cannula when in said first position and delivering oxygen enriched air from the oxygen concentrator to said cylinder filler circuit for filling said cylinder when in said second position, a sensor adapted to detect patient inhalation at said nasal cannula, and a control circuit responsive to the detection of patient inhalation at said nasal cannula for momentarily positioning said flow control valve in said first position to deliver a dose of oxygen enriched air to the patient during such inhalation and then for positioning said flow control valve in said second position for delivering oxygen enriched air to said cylinder filler circuit.

2. Apparatus for filling a cylinder with oxygen enriched air from a medical oxygen concentrator and for delivering oxygen enriched air to a patient, as set forth in claim 1, and wherein said flow control valve is biased to said first position, and wherein said control circuit actuates said flow control valve to move to said second position, whereby said flow control valve defaults to said first position in the event of a failure of said control circuit.

3. Apparatus for filling a cylinder with oxygen enriched air from a medical oxygen concentrator and for delivering oxygen enriched air to a patient, as set forth in claim 1, and wherein said cylinder filler circuit includes an oxygen enriched air accumulator, and a compressor for compressing oxygen enriched air from said accumulator.

4. Apparatus for filling a cylinder with oxygen enriched air from a medical oxygen concentrator and for delivering oxygen enriched air to a patient, as set forth in claim 3, and wherein said compressor is a pressurized gas operated pressure intensifier for filling said cylinder with oxygen enriched air.

5. Apparatus for filling a cylinder with oxygen enriched air from a medical oxygen concentrator and for delivering oxygen enriched air to a patient, as set forth in claim 3, and wherein said compressor is an electric motor operated gas compressor.

6. Apparatus for filling a cylinder with oxygen enriched air from a medical oxygen concentrator and for delivering oxygen enriched air to a patient, as set forth in claim 3, and including a pressure sensor for sensing the pressure in said accumulator, and wherein said control circuit controls operation of said compressor in response to the pressure of oxygen enriched air in said accumulator.

7. Apparatus for filling a cylinder with oxygen enriched air from a medical oxygen concentrator and for delivering oxygen enriched air to a patient, as set forth in claim 6, and wherein said control circuit controls said compressor to maintain a predetermined minimum pressure in said accumulator.

8. Apparatus for filling a cylinder with oxygen enriched air from a medical oxygen concentrator and for delivering oxygen enriched air to a patient, as set forth in claim 3, and further including a pressure regulator and a normally open valve connected between said cylinder and said flow control valve inlet, and means for closing said normally open valve while oxygen enriched air is delivered from an oxygen concentrator to said flow control valve.

9. Apparatus for filling a cylinder with oxygen enriched air from a medical oxygen concentrator and for delivering oxygen enriched air to a patient, as set forth in claim 1, and wherein said cylinder filler circuit includes an oxygen enriched air accumulator, and a chiller for liquefying oxygen enriched air from said accumulator for filling said cylinder with liquefied oxygen enriched air.

10. Apparatus for filling a cylinder with oxygen enriched air from a medical oxygen concentrator and for delivering oxygen enriched air to a patient, as set forth in claim 1, and further including a pressure regulator and a normally open valve connected between said cylinder and said flow control valve inlet, and means for closing said normally open valve while oxygen enriched air is delivered from an oxygen concentrator to said flow control valve.

11. Failsafe apparatus for delivering oxygen enriched air to a patient comprising an oxygen concentrator for producing a flow of oxygen enriched air, a flow controller connected for delivering oxygen enriched air from said oxygen concentrator to a patient, a cylinder for storing oxygen enriched air, a circuit adapted for filling said cylinder with oxygen enriched air from said oxygen concentrator, and wherein said circuit includes means for delivering oxygen enriched air from said cylinder to said flow controller when oxygen enriched air is not delivered from said oxygen concentrator to said flow controller.

12. Failsafe apparatus for delivering oxygen enriched air to a patient, as set forth in claim 11, and wherein said means for delivering oxygen enriched air from said cylinder to said flow controller includes a normally open valve, and means for closing said normally open valve when oxygen enriched air is delivered from said oxygen concentrator to said flow controller.

13. Failsafe apparatus for delivering oxygen enriched air to a patient, as set forth in claim 11, and wherein said flow controller delivers a dose of oxygen enriched air from said oxygen concentrator through a nasal cannula to a patient in response to the beginning of inhalation by the patient, and wherein said flow controller delivers oxygen enriched air from said oxygen concentrator to said cylinder filling circuit when oxygen enriched air is not delivered to the patient.

14. Failsafe apparatus for delivering oxygen enriched air to a patient, as set forth in claim 13, wherein said flow controller delivers a continuous flow of oxygen enriched air to the patient in response to a failure of said flow controller to deliver doses of oxygen enriched air to the patient.

15. A method for providing oxygen enriched air to a patient and to a pressurized gas cylinder comprising the steps of:
  a) supplying a dose of oxygen enriched air from a source of oxygen enriched air to the patient after the patient begins to inhale; and
  b) supplying oxygen enriched air from said source to apparatus for filling a pressurized gas cylinder with oxygen enriched air when a dose of oxygen enriched air is not being delivered to the patient.

16. A method for providing oxygen enriched air to a patient and to a pressurized gas cylinder, as set forth in claim 15, and further including the step of supplying a dose of oxygen enriched air from said pressurized gas cylinder to the patient after the patient begins to inhale when oxygen enriched air is not available from said source.

17. A method for providing oxygen enriched air to a patient and to a pressurized gas cylinder, as set forth in claim 15, and wherein a dose of oxygen enriched air is supplied from a source of oxygen enriched air to the patient only after selected times when the patient begins to inhale.

* * * * *